United States Patent [19]

Wurtman

[11] Patent Number: 5,096,712
[45] Date of Patent: Mar. 17, 1992

[54] METHOD FOR ENHANCING PERFORMANCE SO AS TO IMPROVE VIGOR AND DECREASE FATIGUE, CONFUSION, TENSION, AND ANXIETY

[75] Inventor: Richard J. Wurtman, Boston, Mass.

[73] Assignee: Interneuron Pharmaceuticals, Inc., Lexington, Mass.

[21] Appl. No.: 489,445

[22] Filed: Mar. 6, 1990

[51] Int. Cl.$^5$ ............... A61K 9/20; A61K 31/195; A61K 31/535; A61K 31/42

[52] U.S. Cl. ............... 424/422; 424/439; 424/451; 424/464; 514/231.2; 514/374; 514/561; 514/567; 536/124

[58] Field of Search ............. 514/231.2, 561, 567, 514/374; 536/124; 424/422, 439, 451, 464

[56] References Cited

U.S. PATENT DOCUMENTS

| | | | |
|---|---|---|---|
| 4,327,112 | 4/1982 | Wurtman | 514/567 |
| 4,598,094 | 7/1986 | Wurtman et al. | 514/561 |
| 4,673,689 | 6/1987 | Wurtman et al. | 514/561 |

OTHER PUBLICATIONS

Y. Ito et al., "Selective Cytotoxicity of 4-5-Cysteaminylphenol on Follicular Melanocytes of the Black Mouse: Rational Basis for Its Application to Melanoma Chemotherapy", Cancer Research 47:3278-3284 (1987).

Ito et al., "Depigmentation of Black Guinea Pig Skin by Topical Application of Cysteaminylphenol, Cysteinylphenol, and Related Compounds", The Journal of Investigative Dermatology 88:77-82 (1987).

S. Miura et al., "Synthesis of Cysteinylphenol, Cysteaminylphenol, and Related Compounds, and in Vivo Evaluation of Antimelanoma Effect", Arch Dermatol Res. 279:219-225 (1987).

*Primary Examiner*—Thurman K. Page
*Assistant Examiner*—Carlos Azpuru
*Attorney, Agent, or Firm*—Alan H. Levine

[57] ABSTRACT

A composition for enhancing performance, e.g., improving subjective vigor, decreasing fatigue, diminishing subjective confusion, and decreasing tension and anxiety. The composition comprises an indirect-acting sympathomimetic drug and tyrosine or a tyrosine precursor. The drug may be phenylpropanolamine, amphetamine, or ephedrine. The tyrosine enhances the known performance-enhancing activity of the drug.

5 Claims, No Drawings

METHOD FOR ENHANCING PERFORMANCE SO AS TO IMPROVE VIGOR AND DECREASE FATIGUE, CONFUSION, TENSION, AND ANXIETY

This invention relates to enhancing the performance of individuals by employing indirect-acting sympathomimetic drugs or amines.

A number of such drugs, e.g., phenylpropanolamine, amphetamine, and ephedrine, are traditionally used to enhance performance, e.g., improve subjective vigor, decrease fatigue, diminish subjective confusion, and decrease tension and anxiety, as well as for other purposes. A problem recognized in the past which is associated with use of some indirect-acting sympathomimetic drugs is that after a few doses, they often stop functioning, i.e., tachyphylaxis sets in. U.S. Pat. Nos. 4,598,094 and 4,673,689 deal with this problem and disclose prevention of tachyphylaxis by administering tyrosine or a tyrosine precursor together with indirect-acting sympathomimetic drugs such as ephedrine, phenylpropanolamine, and amphetamine. These patents make no reference whatsoever to combining any of these drugs and tyrosine for performance-enhancing purposes.

The present invention is based on a realization that tyrosine, or a tyrosine precursor, can be used to potentiate the performance-enhancing activity of indirect-acting sympathomimetic drugs.

It is an object of the invention to provide a composition comprising an indirect-acting sympathomimetic drug capable of effecting some enhancement of performance, and tyrosine or a tyrosine precursor.

It is another object of the invention to provide a method of enhancing performance by administering both an indirect-acting sympathomimetic drug capable of effecting some enhancement of performance, and tyrosine or a tyrosine precursor.

The term "indirect-acting sympathomimetic drug" is intended to include within its scope both indirect-acting drugs and mixed-acting drugs having both indirect-acting and direct-acting components. Direct-acting drugs, as their name implies, act directly on sympathomimetic nerve receptors. Indirect-acting drugs cause the nerve cells to release a product which then acts on the nerve receptors.

While the precise mechanism by which the present invention produces the desired function is not entirely clear, it is known that indirect-acting sympathomimetic amine drugs cause nerve endings to release norepinephrine and dopamine. Tyrosine and tyrosine precursors, such as phenylalanine and tyrosine-containing peptides, also can enhance the release of norepinephrine and dopamine from sympathetic neuron synapses. Thus, it is theorized that combining tyrosine or a tyrosine precursor with a sympathomimetic drug produces a synergistic, or at least additive effect, which increase the activity of a given dose of the drug to produce an enhancement of energy, alertness, and relaxation in an individual to whom the drug and tyrosine are administered.

Consequently, the present invention can be used either to increase the performance enhancement effect of such a drug without increasing the amount of the drug which is administered, or the same performance enhancement effect can be obtained by administering a lower dosage of the drug.

Indirect-acting sympathomimetic amine drugs commonly used for effects such as decreasing fatigue, tension, and confusion, and increasing vigor, are phenylpropanolamine (PPA), amphetamine, and ephedrine. Other drugs useful for the purpose are pseudoephedrine, norpseudoephedrine, diethylpropion, benzphetamine, phendimetrazine, phenmetrazine, phentermine, chlorphentermine, and aminorex. For performance enhancement purposes, these drugs are usually administered orally, but in some circumstances they may be administered parenterally, i.e., intravenously, or in any other effective manner, e.g., nasally.

The drugs are administered to a human patient within a preferred range of dosage levels comparable to those found in the standard literature available to practitioners in the field of weight control. For example, PPA is usually administered in dosages of 5 to 25 milligrams (mg) three times per day, i.e., daily dosages of 15 to 75 mg; amphetamine is usually administered in dosages of 1.25 to 10 mg three times per day, i.e., daily dosages of 3.75 to 30 mg; and ephedrine is usually administered in dosages of 5 to 50 mg per day, i.e., daily dosages of 15 to 150 mg. Other drugs used for appetite reduction are administered in dosages as low as 3 mg/day and as high as 150 mg/day.

The amount of tyrosine or tyrosine precursor administered to a human patient is in the range of 250 mg to 15 grams (g), preferably between 1 g and 5 g, per day. Use of less than 250 mg of tyrosine for an adult human is believed to have little or no measurable effect. Dosages of more than 15 g of tyrosine are believed to enter the range in which no appreciable additional advantage is obtained by increases in dosage level. The tyrosine or tyrosine precursor can be administered as free amino acids, peptides, esters, salts, natural or synthetic polymers, or constituents of foods. The route of administration can be oral or parenteral, or any other effective manner. Any suitable tyrosine precursor can be employed, such as a low dose of phenylalanine, i.e., 500 mg or less.

The following examples illustrate that administering tyrosine to a human together with an indirect-acting sympathomimetic amine drug significantly potentiates the performance-enhancing activity of the drug as compared to administration of the drug alone.

EXAMPLE I

The effect of the invention was assessed using a standard test, the POMS test (POM 021) published by Poms Educational and Industrial Service, of San Diego, Calif. 92107. This test sets forth 65 individual words or terms describing certain subjective feelings, e.g. tense, clearheaded, shaky, annoyed, alert, and asks the test-taker to mark one of five boxes which best describes how the test-taker feels right now. The five boxes are labeled "not at all", "a little", "moderately", "quite a bit", and "extremely".

An adult male subject took the POMS test three times at intervals of three to four days between tests. Each of the three tests was taken one to two hours after the subject received (1) a placebo; (2) a single 25 milligram dose of PPA alone; (3) a single dose comprising 25 mg of PPA and 2 grams of tyrosine.

The test taken after administration of PPA alone revealed a small improvement in some of the indices as compared to the test taken after administration of the placebo. For example, there was some increase in vigor and reduction in confusion, but not in tension, and there was no elevation in mood, i.e., responses to "grouchy", "blue", and "discouraged" remained the same for both tests (placebo and PPA alone). However, the test taken after administration of PPA and tyrosine revealed significant improvement in almost every response to the 65 feelings set forth in the test. For example, the response to "energetic" changed from "a little" (placebo) to "quite a bit" (PPA plus tyrosine); "worn out" changed from "moderately" to "not at all"; "confused" changed from "moderately" to "not at all"; "tense" changed from "moderately" to "a little".

EXAMPLE II

The same POMS test was used, and the same procedure was used with an adult male subject, as in Example I, except that ephedrine was substituted for PPA, and the dose of ephedrine was 50 mg.

The results were substantially the same as those of Example I.

The invention has been shown and described in preferred form only, and by way of example, and many variations may be made in the invention which will still be comprised within its spirit. It is understood, therefore, that the invention is not limited to any specific form or embodiment except insofar as such limitations are included in the appended claims.

I claim:

1. A method of enhancing performance of an individual, which includes any one or more of improving vigor, and decreasing fatigue, confusion, tension, and anxiety, by administration of an indirect-acting sympathomimetic drug so as to produce a greater performance-enhancing effect than that produced by administration of the drug alone, comprising administering to the individual an indirect-acting sympathomimetic drug capable of effecting said enhancement of performance, and tyrosine or a tyrosine precursor, the drug and tyrosine being administered in an amount equal to 1.25 to 150 mgs of the drug and 250 mgs to 15 grams of tyrosine, per day.

2. A method as defined in claim 1 wherein the tyrosine precursor is a tyrosine-containing peptide.

3. A method as defined in claim 1 wherein the indirect-acting sympathomimetic drug is selected from the group consisting of ephedrine, amphetamine, phenylpropanolamine, pseudoephedrine, norpseudoephedrine, diethylpropion, benzphetamine, phendimetrazine, phenmetrazine, phentermine, chlophentermine, aminorex, and combinations thereof.

4. A method as defined in claim 1 wherein the indirect-acting sympathomimetic drug is selected from the group consisting of phenylpropanolamine, amphetamine, and ephedrine, and combinations thereof.

5. A method as defined in claim 1 wherein the ratio of tyrosine or tyrosine precursor to the indirect-acting sympathomimetic drug is a therapeutically effective amount large enough to increase the performance-enhancing effect of the drug.

* * * * *